US010260300B2

(12) United States Patent
Dorovsky et al.

(10) Patent No.: US 10,260,300 B2
(45) Date of Patent: Apr. 16, 2019

(54) MEASURING FORMATION POROSITY AND PERMEABILITY

(71) Applicant: BAKER HUGHES, A GE COMPANY, LLC, Houston, TX (US)

(72) Inventors: Vitaly Nikolaevich Dorovsky, Novosibirsk (RU); Yury Vadimovich Perepechko, Novosibirsk (RU); Maxim Yurievich Podberezhny, Moscow (RU)

(73) Assignee: Baker Hughes, a GE Company LLC, Houston, TX (US)

( * ) Notice: Subject to any disclaimer, the term of this patent is extended or adjusted under 35 U.S.C. 154(b) by 119 days.

(21) Appl. No.: 15/101,569

(22) PCT Filed: Dec. 4, 2013

(86) PCT No.: PCT/RU2013/001088
§ 371 (c)(1),
(2) Date: Jun. 3, 2016

(87) PCT Pub. No.: WO2015/084206
PCT Pub. Date: Jun. 11, 2015

(65) Prior Publication Data
US 2016/0299050 A1 Oct. 13, 2016

(51) Int. Cl.
E21B 25/00 (2006.01)
G01N 1/08 (2006.01)
G01N 33/24 (2006.01)
G01V 1/00 (2006.01)
G01N 15/08 (2006.01)
(Continued)

(52) U.S. Cl.
CPC ............ E21B 25/00 (2013.01); E21B 10/02 (2013.01); E21B 47/06 (2013.01); E21B 49/02 (2013.01);
(Continued)

(58) Field of Classification Search
CPC .......... E21B 10/02; E21B 25/00; E21B 25/06; E21B 3/00; E21B 47/06; E21B 49/02
See application file for complete search history.

(56) References Cited

U.S. PATENT DOCUMENTS 3,901,075 A   8/1975   Hampton et al.
6,003,620 A   12/1999  Sharma et al.
(Continued)

FOREIGN PATENT DOCUMENTS

WO   2009042774 A2   4/2009
WO   2013032355 A2   3/2013

OTHER PUBLICATIONS

PCT/RU2013/001088 International Preliminary Report on Patentability dated Jun. 15, 2016; 7 pages.
(Continued)

Primary Examiner — Caroline N Butcher
(74) Attorney, Agent, or Firm — Bracewell LLP; Keith R. Derrington

(57) ABSTRACT

Values for porosity and permeability of core samples in a borehole are estimated by generating radial waves with an acoustic source in fluid around the core sample, and measuring pressure in the fluid. Moreover, the acoustic source operates at frequency close to a resonant frequency of the core sample. After the acoustic source no longer operates at the resonant frequency, pressure in the fluid attenuates over time. The pressure attenuation is recorded by the pressure measurements, along with the pressure in the fluid at the first harmonic (spectral component). The pressure attenuation and spectral component each are dependent on porosity and permeability of the core sample. Thus values for the porosity and permeability are determined based on the arithmetic relationships between pressure attenuation and the spectral component and porosity and permeability.

15 Claims, 3 Drawing Sheets

(51) Int. Cl.
*G01V 1/50* (2006.01)
*E21B 10/02* (2006.01)
*E21B 47/06* (2012.01)
*E21B 49/02* (2006.01)
*G01V 1/48* (2006.01)
*E21B 3/00* (2006.01)
*E21B 25/06* (2006.01)

(52) U.S. Cl.
CPC ............... *G01N 1/08* (2013.01); *G01N 15/08* (2013.01); *G01N 15/0826* (2013.01); *G01N 33/24* (2013.01); *G01V 1/00* (2013.01); *G01V 1/48* (2013.01); *G01V 1/50* (2013.01); *E21B 3/00* (2013.01); *E21B 25/06* (2013.01); *G01V 2210/1299* (2013.01); *G01V 2210/1429* (2013.01); *G01V 2210/6244* (2013.01); *G01V 2210/6246* (2013.01)

(56) References Cited

U.S. PATENT DOCUMENTS

2011/0242938 A1\* 10/2011 Garcia-Osuna ......... E21B 49/06
367/86
2012/0041680 A1 2/2012 Dorovsky et al.

OTHER PUBLICATIONS

Sinev, A.V., et al "Additional Acoustic Method for Measuring Formation Permeability in the Presence of Mudcake Achieved," SPE Russian Oil and Gas Exploration and Production Technical Conference and Exhibition, Oct. 16-18, Moscow, Russia, Society of Petroleum Engineers.
PCT/RU2013/001088 International Search Report and Written Opinion dated Sep. 15, 2014, 11 pages.

\* cited by examiner

MEASURING FORMATION POROSITY AND PERMEABILITY

CROSS REFERENCE TO RELATED APPLICATION

This application is a U.S. National Stage Application of International Application No. PCT/RU2013/001088 filed Dec. 4, 2013, which designates the United States and which is incorporated herein by reference in its entirety.

BACKGROUND OF THE INVENTION

1. Field of Invention

The present disclosure relates in general to a method of estimating parameters of a subterranean formation. More specifically, the present disclosure relates to a method of estimating porosity and/or permeability of a subterranean formation by measuring a spectral component of a resonant frequency of a sample of the formation.

2. Description of Prior Art

A hydrocarbon production rate and overall yield in a subterranean formation can be estimated based on the porosity and permeability of the strata making up the formation. Sometimes a coring tool is used to extract rock samples from within the formation and bring the samples to surface where properties of the sample are measured. Characteristics of the formation, such as porosity and permeability, can be estimated based on values of the measured properties.

However, while the core sample is being pulled to the surface, the hydrostatic pressure decreases gradually allowing gas to come out of solution inside the core. During its escape from the core, the expanding gas drives the formation fluids expelling oil and/or water out of pores. spaces, and cracks in the core. Standard core analysis thus cannot obtain accurate information about the in situ condition of the core and any entrained fluids, and thus is generally not used to properly quantify fluid parameters.

SUMMARY OF THE INVENTION

Disclosed herein is a method of evaluating porosity and permeability of subterranean rock formation by analyzing a core sample downhole. In an example, a method of estimating characteristics of a core sample in a borehole includes measuring values of pressure in a fluid surrounding the core sample that fluctuate in response to radial waves that propagate through the fluid and the core sample, identifying an attenuation of pressure in the fluid over time based on the measured pressure; identifying a pressure in the fluid at the frequency of a resonant peak, and estimating at least one of porosity or permeability of the core sample based on the values of pressure and pressure attenuation. The radial waves can be at a frequency which is at about a resonant frequency of the core sample. In this example, the step of identifying an attenuation of pressure in the fluid can take place after radial waves at the resonant frequency of the core sample no longer propagate through the fluid. The method can further include providing an acoustic source for generating the radial waves. Optionally, the acoustic source operates at about the first resonant frequency of the core sample. The resonant peak may optionally be at the first resonant peak. In an alternative, the core sample is obtained with a coring tool, and wherein the step of measuring values of pressure takes place in the coring tool.

Also disclosed herein is a method of estimating characteristics of a core sample in a borehole that includes obtaining the core sample with a coring tool in the borehole and immersing the core sample with a liquid, radial waves are generated in the liquid with a transmitter that operates at a resonant frequency of the core sample, an attenuation of peaks of pressure in the fluid over time are identified, where pressure peaks are from the radial waves that come from the core sample. The method further includes identifying a pressure in the fluid at the frequency of a resonant peak that is from at least one of the radial waves and estimating at least one of porosity or permeability of the core sample. The step of estimating at least one of porosity or permeability of the core sample can be based on the identifying the pressure attenuation or pressure peak. The method may further optionally include terminating generating radial waves at the resonant frequency prior to measuring the pressure attenuation. In one example, the resonant frequency of the core sample is estimated.

Further disclosed herein is a system for estimating characteristics of a core sample in a borehole and which is made up of a coring bit having an axial bore in which the core sample is selectively disposed, a tubular transducer that circumscribes the axial bore and selectively oscillates at about the resonant frequency of the core sample, an acoustic receiver disposed in the axial bore and immersed in liquid that contacts the core sample, and that selectively receives radial waves generated by the transducer that reflect from the core sample. The system may further include a processor for estimating a value for at least one of a porosity or permeability of the core sample based on a measurement of an attenuation of pressure of the radial waves received by the receiver and a pressure measured in the fluid at a first resonant frequency of the core sample. The system can further have springs for suspending the receiver in the fluid. Optionally included with the system is a housing on which the coring bit is attached and which defines a coring tool; in this example a drill string can be attached to an end of the coring tool for rotating the coring bit. The liquid can be disposed in the axial bore when the coring bit is at surface.

BRIEF DESCRIPTION OF DRAWINGS

Some of the features and benefits of the present invention having been stated, others will become apparent as the description proceeds when taken in conjunction with the accompanying drawings, in which.

Figure 1:
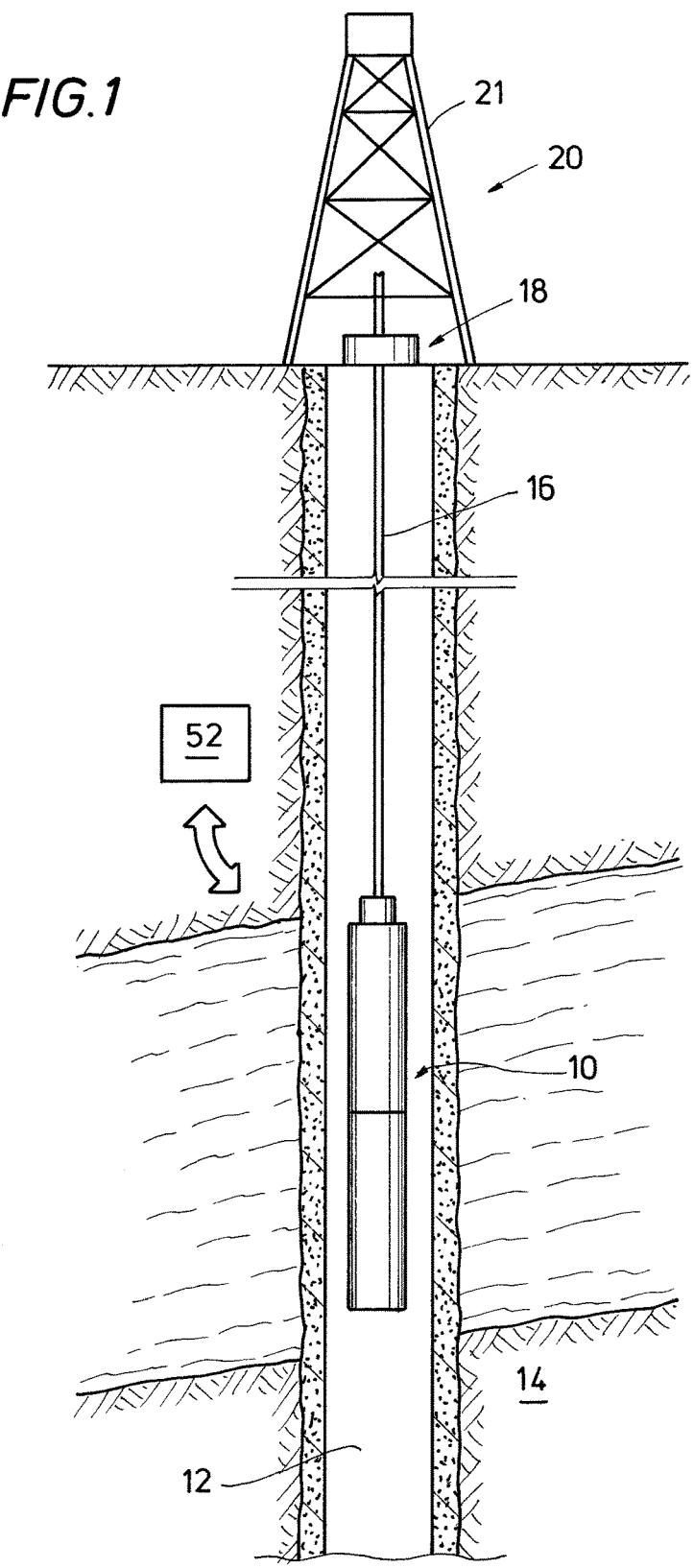
FIG. 1 is a side partial sectional view of an example of a coring tool deployed in a wellbore and in accordance with the present invention.

While the invention will be described in connection with the preferred embodiments, it will be understood that it is not intended to limit the invention to that embodiment. On the contrary, it is intended to cover all alternatives, modifications, and equivalents, as may be included within the spirit and scope of the invention as defined by the appended claims.

DETAILED DESCRIPTION OF INVENTION

The method and system of the present disclosure will now be described more fully hereinafter with reference to the accompanying drawings in which embodiments are shown. The method and system of the present disclosure may be in many different forms and should not be construed as limited to the illustrated embodiments set forth herein; rather, these embodiments are provided so that this disclosure will be thorough and complete, and will fully convey its scope to those skilled in the art. Like numbers refer to like elements throughout.

It is to be further understood that the scope of the present disclosure is not limited to the exact details of construction, operation, exact materials, or embodiments shown and described, as modifications and equivalents will be apparent to one skilled in the art. In the drawings and specification, there have been disclosed illustrative embodiments and, although specific terms are employed, they are used in a generic and descriptive sense only and not for the purpose of limitation.

Shown in side sectional view in FIG. 1 is an example of a coring tool 10 disposed in a borehole 12 that intersects a subterranean formation 14. The coring tool 10 is deployed on a lower end of a drill string 16. A rotary table 18 couples with the drill string 16 on surface and rotates the drill string 16 so the coring tool 10 can bore into the formation 14 and obtain core samples from the formation 14. The rotary table 18 is included as part of a drilling rig 20 on the surface shown having a derrick 21 for supporting the rotary table 18 and drill string 16.

Figure 2:
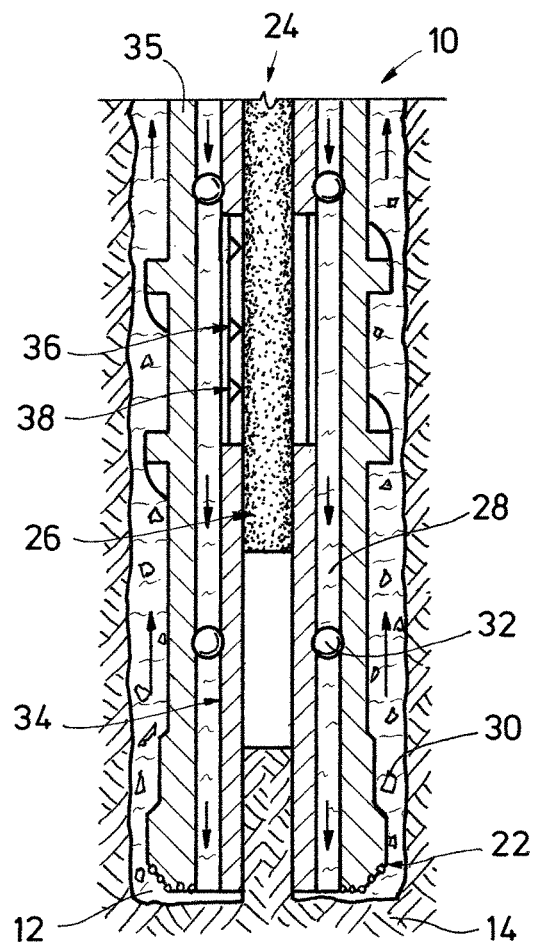
FIG. 2 is a side sectional view of an example of a portion of the coring tool of FIG. 1 obtaining core samples in a wellbore and in accordance with the present invention.

Referring now to FIG. 2, shown in side sectional view is a detailed portion of the coring tool 10 in the borehole 12 illustrating that a bit 22 is included on a lower end of the coring tool 10 for excavating in the formation 14. An elongate bore 24 extends axially through the bit 22, and in which a core sample 26 is received after the bit 22 excavates the rock surrounding the core 26. Drilling fluid or mud can be circulated downhole through the coring tool 10 within an annulus 28 shown extending axially through the bit 22 and spaced radially outward from the bore 24. In addition to cooling the bit 22 during excavating, the drilling fluid washes cuttings 30 back uphole that were removed from the formation 14 by the cutting action of the bit 22.

Optional bearings 32 are shown in the annulus 28 and between an inner body 34 and outer tubing 35. Both the inner body 34 and outer tubing 35 are tubular members, where the inner body 34 is coaxially and rotationally set within the outer tubing 35. The inner body 34 contains the core sample 26, and the outer tubing 35 defines an outer surface of the annulus 28 and includes cutting elements on its outer surface for cutting through the formation 14.

Also disposed in the annulus 28 is a transmitter 36 for generating an acoustic signal; in one example the signal includes a radial wave R (FIG. 3) that contacts, passes through, and reflects from the sample 26. A receiver 38, which in one example can be a hydrophone, is illustrated spaced axially away from the transmitter 36. Examples exist wherein the transmitter 36 and receiver 38 are integrated into a single unit. In an example, the inner body 34 is filled with a selected known fluid before being deployed downhole. Optionally, an elastic liner (not shown) can be provided on an inner surface of the inner body 34 for preventing damage to the sample core 26 and to prevent formation fluids from escaping the sample core 26 or from within the bore 24.

Figure 3:
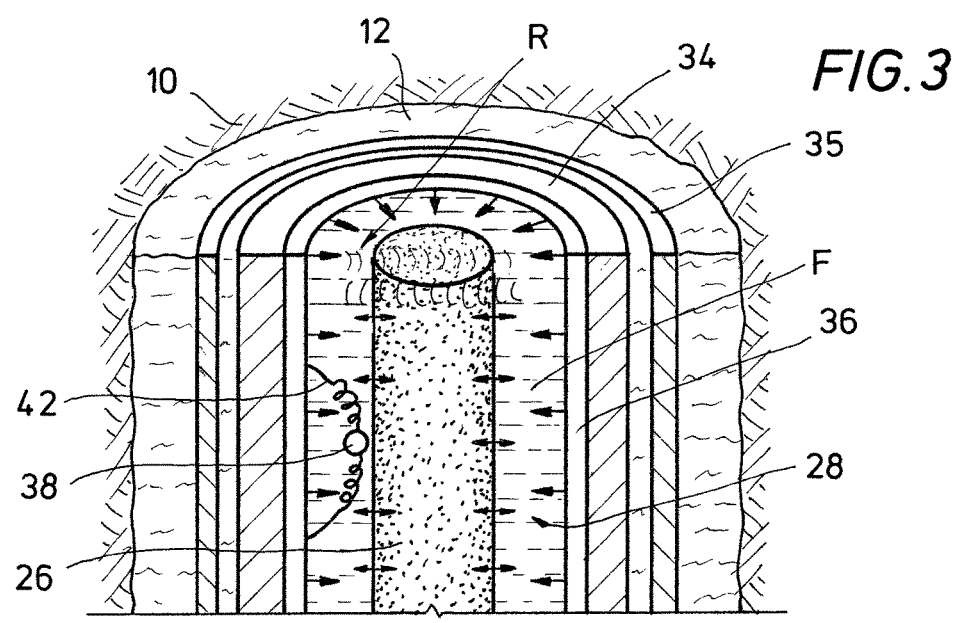
FIG. 3 is a side sectional perspective view of an embodiment of acoustically measuring a core sample in the coring tool of FIG. 2 and in accordance with the present invention.

Schematically illustrated in side sectional perspective view in FIG. 3 are radial acoustic waves R being generated in fluid F that surrounds the core sample 26, and where reflections of the radial waves R from the core sample 26 are recorded by the receiver 38. As illustrated in the example of FIG. 3, the transmitter 36 is a tubular member that is selectively oscillated to generate the radial acoustic waves R in the fluid F. Example materials for the transmitter 36 include piezoelectric and/or magnetostrictive materials, in an example the transmitter 36 is oscillated by applying electricity to the transmitter 36.

Also shown in FIG. 3 is that the hydrophone 38 is suspended in the annulus 28 and supported by springs 42. In a non-limiting example, the transmitter 36 is operated at the resonant frequency of the radial eigenwaves of the core sample 26; which in one embodiment is at a frequency that is within about +/−5% of the first resonant frequency. Further in this example, the receiver 38 records the pressure of the radial acoustic wave R. Where in one example, the pressure of the radial acoustic wave is the increase in pressure due to the compressional waves.

Referring back to FIG. 2, in one non-limiting example of operation, the coring tool 10 is rotated in the borehole 12 so that the bit 22 excavates an annular cut into the formation 14 thereby forming the core sample 26 that extends into the bore 24. The transmitter 36 is actuated for a period of time to generate radial waves R (FIG. 3) shown in the fluid F propagating towards the core sample 26. A portion of the radial waves R reflect from the core sample 26 and are measured by the receiver 38; as indicated above the receiver 38 records the pressure of the radial acoustic wave R reflected from the core sample 26.

Figure 4:
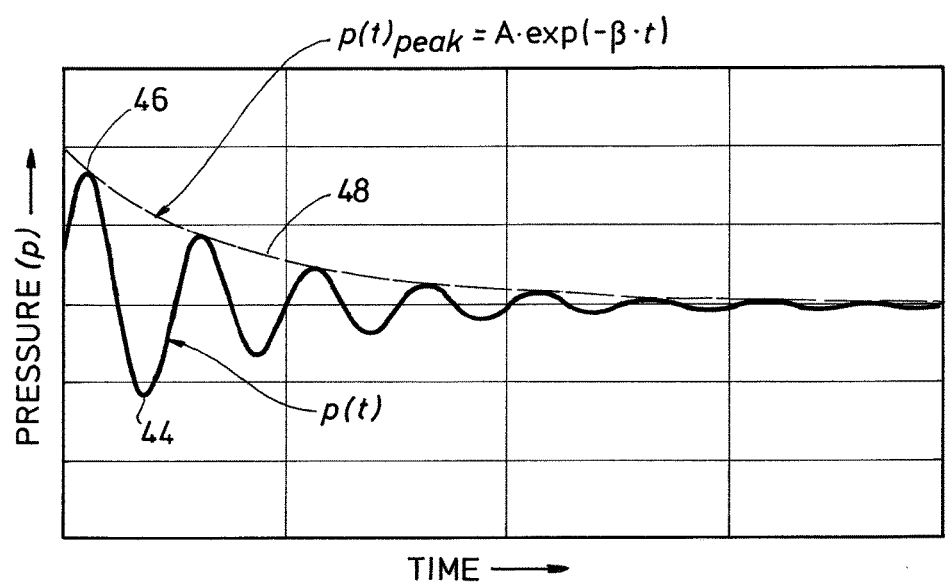
FIG. 4 is an example plot of pressure wave attenuation of an acoustic signal adjacent a core sample and in accordance with the present invention.

Referring now to FIG. 4, shown is a plot 44 that represents pressure in the fluid F measured by the receiver 38, where the recorded pressure is a result of the acoustic signal in the fluid F generated by the transmitter 36. Shown in FIG. 4 is that the peaks 46 of the measured pressure decay over time. The decay of the pressure peaks 46 are modeled by plot 48, which is represented by the expression $Ae^{(-\beta t)}$. In one embodiment, the measured pressure decay over time takes place after the transmitter 36 no longer operates at the resonant frequency. It has been found that the attenuation factor of the pressure waves (the envelope of the maximal values of pressure) is also determined by permeability k and porosity φ of the formation, where:

$$\beta = \varphi(k, \varphi) \qquad \text{Equation (1).}$$

Figure 5:
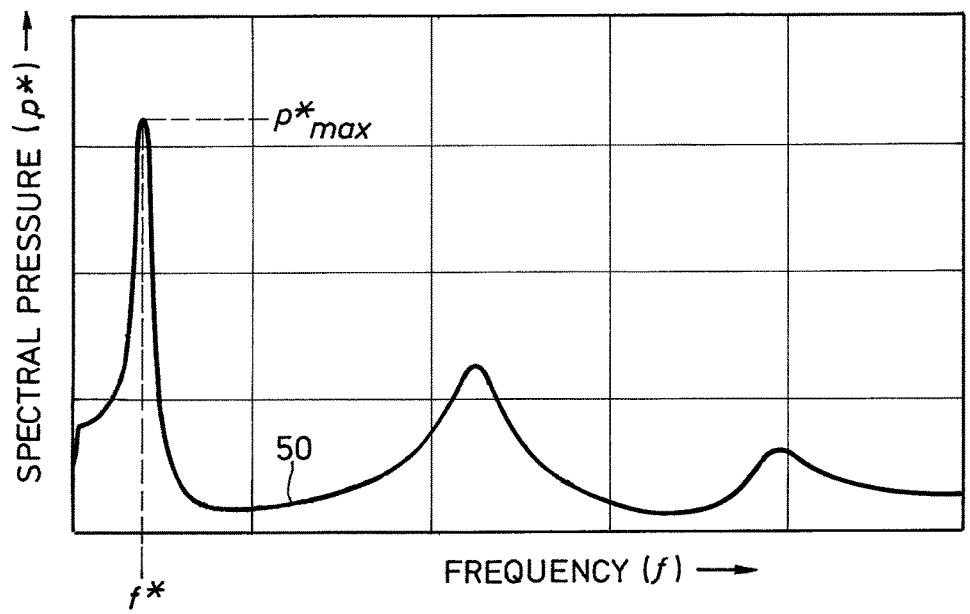
FIG. 5 is an example plot of eigenwaves of an acoustic signal adjacent a core sample and in accordance with the present invention.

Shown in FIG. 5 is a plot 50 that represents a spectrum of sample eigenwaves. Analyzing the behavior of spectral component of pressure at the harmonic source at the minimal resonant frequency can yield useful information. For example, it has been found that the value of pressure at the first maximum (pressure at the frequency of the first resonant peak) is dependent upon formation permeability k and porosity φ, where:

$$p_{max} = \psi(k, \varphi) \qquad \text{Equation (2).}$$

Equations (1) and (2) at given acoustic velocities in fluid and the formation, at corresponding porosities, constitute a set of equations for finding permeability and porosity. Measuring $p_{max}$ and β and solving sets (1), (2), values can be obtained for permeability k and porosity φ. Provided below are how the functional dependences φ(k, φ) and $p_{max}=$ ψ(k, φ) were theoretically obtained.

Functions φ(k, φ), ψ(k, φ) are found from the theory describing the radial waves in the borehole with saturated porous core sample. The acoustic equations of the two-velocity medium are a linearized version of the following equations, where Equations (3)-(7) describe the propagation of waves in the saturated porous core sample:

$$\frac{\partial \rho}{\partial t} + div j = 0, \quad \text{Equation (3)},$$

$$\frac{\partial g_{ik}}{\partial t} + g_{jk}\partial_i u_j + g_{ij}\partial_k u_j + u_j\partial_j g_{ik} = 0, \quad \text{Equation (4)},$$

$$\frac{\partial j_i}{\partial t} + \partial_k(\rho_s u_i u_k + \rho_l v_i v_k + p\delta_{ik} + g_{jk}h_{ij} + \pi_{ik}) = 0, \quad \text{Equation (5)},$$

$$\frac{\partial v_i}{\partial t} + (v, \nabla)v_i =$$
$$-\frac{1}{\rho}\partial_i p + \frac{\rho_s}{2\rho}\partial_i(u-v)^2 - \frac{1}{2\rho}h_{jk}\partial_i g_{jk} + \frac{1}{\rho_l}f_i, \quad \text{Equation (6)},$$

and $$\frac{\partial S}{\partial t} + div\left(S\frac{j}{\rho} + \frac{q}{T}\right) = \frac{R}{T}. \quad \text{Equation (7)}.$$

The condition of the positive dissipative function R is as follows:

$$-R = f\frac{1}{\rho_l}(j - \rho u) + q\frac{\nabla T}{T} + A_{ik}\left(\partial_i v_k + \partial_k v_i - \frac{2}{3}\delta_{ik} div v\right) + a div v, \quad \text{Equation (8)}$$

and it determines the form of the dissipative flows:

$$q = \alpha_{12}(\rho u - j) + \kappa\frac{1}{T}\nabla T, \quad \text{Equation (9)},$$

$$f + \partial_k \pi_{ik} = b(\rho u - j) + \rho_l \alpha_{12}\frac{1}{T}\nabla T, \quad \text{Equation (10)},$$

and $$\pi_{ik} = A_{ik} + a\delta_{ik}, \quad \text{Equation (11)}.$$
$$A_{ik} = -\eta\left(\partial_i v_k + \partial_k v_i - \frac{2}{3}\delta_{ik} div v\right),$$
$$a = -\zeta div v.$$

The equation of the state of the saturated porous medium is selected in the following form:

$$p = p_0 - \frac{1}{2}Kg_{ll} + \frac{1}{\rho_0}(K+\gamma)\rho + \alpha_p S + \frac{1}{2}\rho_s(u-v)^2, \quad \text{Equation (12)},$$

$$T = T_0 + \alpha_s S + \alpha_p \frac{1}{\rho_0}\rho, \quad \text{Equation (13)},$$

and $$h_{ik} = h_{0,ik} + \mu g_{ik} + \frac{1}{2}\lambda g_{ll}\delta_{ik} - \frac{\rho}{\rho_0}Kg_{ll}\delta_{ik} - \frac{1}{2}g^{ik}\rho_s(u-v)^2. \quad \text{Equation (14)}.$$

In the formulae above, $\rho_l$, $\rho_s$ are partial densities of the saturating fluid and porous matrix, respectively, $\rho = \rho_l + \rho_s$ is density of the saturated medium; u, v are velocities of the porous matrix and saturating fluid; $j = \rho_s u + \rho_l v$ is the momentum; $h_{ik}$ is the stress tensor, $g_{ik}$ is the metric tensor; p is pressure, T is temperature, S is entropy; λ, μ and γ are elastic moduli of the saturated porous medium; $\alpha_s$, $\alpha_p$ are thermodynamic parameters of the medium. The dissipative coefficient of the interphase friction b may be found from the ratio $b=\eta/(k\rho)$, where η is dynamic viscosity of saturating fluid, k is permeability of the porous medium.

The linearized isothermal version of Equations (3)-(6) enables one to find the motion equations of the porous matrix u and saturating fluid v in the acoustic approximation:

$$\frac{\partial^2 u}{\partial t^2} - c_t^2 \Delta u - a_1 \nabla div u + a_2 \nabla div v + \frac{\rho_l}{\rho_s}b\left(\frac{\partial u}{\partial t} - \frac{\partial v}{\partial t}\right) = 0, \quad \text{Equation (15)},$$

and $$\frac{\partial^2 v}{\partial t^2} + a_3 \nabla div u - a_4 \nabla div v - b\left(\frac{\partial u}{\partial t} - \frac{\partial v}{\partial t}\right) = 0. \quad \text{Equation (16)}.$$

Coefficients $a_i$ (i=1, . . . , 4) are determined by the elastic moduli of the saturated porous medium λ, μ and γ:

$$a_1 = \frac{1}{\rho_s}\left(\frac{\rho_s^2}{\rho^2}\gamma + \frac{\rho_l^2}{\rho^2}K + \frac{1}{3}\mu\right), \quad \text{Equation (17)},$$

$$a_2 = \frac{\rho_l}{\rho_s}\left(\frac{\rho_l}{\rho^2}K - \frac{\rho_s}{\rho^2}\gamma\right),$$

and $$a_3 = \frac{\rho_l}{\rho^2}K - \frac{\rho_s}{\rho^2}\gamma, \quad \text{Equation (18)}.$$

$$a_4 = \frac{\rho_l}{\rho_s}K + \frac{\rho_l}{\rho^2}\gamma,$$

The three moduli K, μ and γ, where $K=\lambda+2\mu/3$, may be found from three acoustic velocities $c_{p1}$, $c_{p2}$, $c_t$ of the ideal hydrodynamic approximation, in accordance with the formulae given below:

$$\mu = \rho_s c_t^2, \quad \text{Equation (19)},$$

$$\lambda = \frac{1}{2}\frac{\rho_s}{\rho_l}\left(\rho c_{p1}^2 + \rho c_{p2}^2 - 4\rho_l c_t^2 - \sqrt{(\rho c_{p1}^2 + \rho c_{p2}^2) - \frac{64}{9}\rho_s\rho_l c_t^4}\right),$$

and $$\gamma = \frac{1}{2}\left(\rho c_{p1}^2 + \rho c_{p2}^2 - \frac{8}{3}\rho_s c_t^2 + \sqrt{(\rho c_{p1}^2 + \rho c_{p2}^2) - \frac{64}{9}\rho_s\rho_l c_t^4}\right). \quad \text{Equation (20)}.$$

The acoustic field in borehole fluid is described by the following equation:

$$\frac{\partial^2 v}{\partial t^2} = c_{p0}^2 \nabla div v = 0, \quad \text{Equation (21)}.$$

Where $c_{p0}$ is the velocity of sound in borehole fluid.

The following boundary conditions are shown in FIG. 3:
(1) On the surface of the acoustic transmitter, the source with the amplitude $p^{(0)}=p_0(t)$ is given; (2) At the boundary between the borehole and saturated porous sample, the continuity condition is applied to the mass flow, stress tensor $\Sigma_{rr}$, and partial pressures: $(1-\phi)u_r^{(1)}+\phi v_r^{(1)}=v_r^{(0)}$, $\Sigma_{rr}^{(1)}=\Sigma_{rr}^{(0)}$, $p^{(1)}/\rho^{(1)}=p^{(0)}/\rho^{(0)}$ where $\phi$ is porosity. The latter condition follows from a more general continuity condition of the partial stress tensor in fluid $\Sigma_{rr}^{l(1)}=\phi\Sigma_{rr}^{(0)}$, where $\Sigma_{rr}^{(1)}=\Sigma_{rr}^{s(1)}+\Sigma_{rr}^{l(1)}$.

Time derivatives of stress tensor components and pressure can be found via the displacement velocities:

$$-\frac{\partial p^{(1)}}{\partial t} = d_1 div u^{(1)} + d_2 div v^{(1)}, \quad \text{Equation (22),}$$

$$\frac{\partial \Sigma_{rr}^{(1)}}{\partial t} = d_3 div u^{(1)} + d_4 div v^{(1)} + 2d_5 u_r', \quad \text{Equation (23),}$$

and $$\frac{\partial \Sigma_{rr}^{(0)}}{\partial t} = -\frac{\partial p^{(0)}}{\partial t} = d_0 div v^{(0)}, \quad \text{Equation (24).}$$

Where: $d_1=(\rho_s^{(1)}\gamma-\rho_l^{(1)}K)/\rho^{(1)}, d_2=(\rho_l^{(1)}\gamma+\rho_l^{(1)}K)/\rho^{(1)}$, Equation (25)

$d_3=\rho_s^{(1)}\gamma/\rho^{(1)}-2\mu/3, d_4=\rho_l^{(1)}\gamma/\rho^{(1)}$, Equation (26), and $\pi_5=\mu, \pi_0=\rho^{(0)}c_{p0}^2$. Equation (27).

The set of equations presented with corresponding boundary conditions was solved numerically. The result is the functional dependences $\phi(k, \phi)$, $\psi(k, \phi)$.

Referring back to FIG. 1, a controller 52 is shown in communication with the coring tool 10, wherein the controller 52 can be housed within the coring tool 10 or on surface. In an example, the controller 52 receives the values of pressure measured in the coring tool 10. Yet further optionally, the controller 52 is equipped with a processor for calculating the values of porosity and/or permeability as described above. The controller 52 may include an information handling system (IHS), where the IHS optionally includes one or more of a processor, memory accessible by the processor, nonvolatile storage area accessible by the processor, and logics for performing each of the steps above described.

The present invention described herein, therefore, is well adapted to carry out the objects and attain the ends and advantages mentioned, as well as others inherent therein. While a presently preferred embodiment of the invention has been given for purposes of disclosure, numerous changes exist in the details of procedures for accomplishing the desired results. These and other similar modifications will readily suggest themselves to those skilled in the art, and are intended to be encompassed within the spirit of the present invention disclosed herein and the scope of the appended claims.

What is claimed is:

1. A method of estimating characteristics of a core sample in a borehole comprising:
   (a) measuring values of pressure in a fluid surrounding the core sample that fluctuate in response to radial waves that propagate radially through the fluid and reflect from the core sample;
   (b) identifying an attenuation of pressure in the fluid over time based on step (a);
   (c) identifying a pressure in the fluid at a resonant frequency of the core sample; and
   (d) estimating at least one of porosity or permeability of the core sample based on the values identified in steps (b) and (c).

2. The method of claim 1, wherein the radial waves are at a frequency at about a resonant frequency of the core sample.

3. The method of claim 2, wherein the step of identifying an attenuation of pressure in the fluid takes place after radial waves at the resonant frequency of the core sample no longer propagate through the fluid.

4. The method of claim 1, wherein the fluid comprises a known fluid, and that is isolated from a wellbore fluid that is disposed in the borehole.

5. The method of claim 1, further comprising generating the radial waves with an acoustic source that operates at about the first resonant frequency of the core sample, wherein the acoustic source is a tubular member that circumscribes the core and the fluid, and comprises a material selected from the group consisting of a piezoelectric material, a magnetostrictive material, and combinations thereof.

6. The method of claim 1, wherein the resonant frequency is a minimal resonant frequency.

7. The method of claim 1, further comprising obtaining the core sample with a coring tool, and wherein step (a) takes place in the coring tool.

8. A method of estimating characteristics of a core sample in a borehole comprising:
   (a) obtaining the core sample with a coring tool in the borehole and immersing the core sample in a fluid;
   (b) using a transmitter that operates at a resonant frequency of the core sample to generate radial waves in the fluid that propagate radially through the fluid and reflect from the core sample;
   (c) identifying an attenuation of peaks of pressure in the fluid over time that are from the radial waves that propagate through the core sample;
   (d) identifying a pressure in the fluid at the frequency of a resonant peak that is from at least one of the radial waves; and
   (e) estimating at least one of porosity or permeability of the core sample.

9. The method of claim 8, wherein the step of estimating at least one of porosity or permeability of the core sample is based on the steps of identifying of steps (b) and (c).

10. The method of claim 8, further comprising the generation of radial waves at the resonant frequency is terminated prior to steps (c) and (d).

11. The method of claim 8, wherein the resonant frequency of the core sample is estimated.

12. A system for estimating characteristics of a core sample in a borehole comprising:
   a coring bit having an axial bore in which the core sample is selectively disposed;
   a tubular transducer that circumscribes the axial bore and selectively oscillates at about a resonant frequency of the core sample;
   an acoustic receiver disposed in the axial bore and immersed in a fluid that contacts the core sample, and that selectively receives radial waves generated by the tubular transducer that propagate radially through the fluid and reflect from the core sample; and
   a processor for estimating a value for at least one of a porosity or permeability of the core sample based on a measurement of an attenuation of pressure of the radial waves received by the receiver and a pressure measured in the fluid at the resonant frequency of the core sample.

13. The system of claim 12, further comprising springs for suspending the acoustic receiver in the fluid.

14. The system of claim 12, further comprising a housing on which the coring bit is attached and which defines a coring tool, and a drill string attached to an end of the coring tool for rotating the coring bit.

15. The system of claim 12, wherein the fluid is disposed in the axial bore when the coring bit is at surface, and wherein the fluid has known properties and is isolated from drilling fluid that is selectively circulated through the system.

\* \* \* \* \*